(12) United States Patent
Kayajanian

(10) Patent No.: US 6,444,698 B1
(45) Date of Patent: Sep. 3, 2002

(54) APPLICATION OF 2,3,7,8-TETRACHLORODIBENZO-PARA-DIOXIN (TCDD) AS A PROMOTER BLOCKER OF CANCER

(76) Inventor: Gary Michael Kayajanian, 1600 S. Joyce St., Suite 1411, Arlington, VA (US) 22202

( * ) Notice: Subject to any disclaimer, the term of this patent is extended or adjusted under 35 U.S.C. 154(b) by 0 days.

(21) Appl. No.: 09/925,449

(22) Filed: Aug. 10, 2001

Related U.S. Application Data

(63) Continuation-in-part of application No. 09/501,514, filed on Feb. 9, 2000, now abandoned, which is a continuation-in-part of application No. 09/167,967, filed on Oct. 8, 1998, now abandoned.

(51) Int. Cl.$^7$ .............................................. A61K 31/335
(52) U.S. Cl. ....................... 514/452; 514/454; 514/468; 514/908
(58) Field of Search ................................ 514/452, 454, 514/468, 908

(56) References Cited

U.S. PATENT DOCUMENTS 5,516,790 A * 5/1996 Safe ........................... 514/443

OTHER PUBLICATIONS

DiGiovanni et al, "2,3,7,8–Tetrachlorodibenzo–p–Dioxin: Potent Anticarcinogenic Activity in CD–1 Mice", Biochemical and Biophysical Research Communications, vol. 86, No. 3, ppl. 557–584 (1979).*

DiGiovanni et al, "2,3,7,8–Tetrachlorodibenzo–p–Dioxin (TCDD)–Induced Alterations in Oxidative and Nonoxidative Biotransformation of PAH in Mouse Skin: Role in Anticarcinogenesis by TCDD", Chem. Biol. Eff. Intl. Symp. 4$^{th}$ (1980).*

* cited by examiner

*Primary Examiner*—Frederick Krass

(57) ABSTRACT

This Invention relates to the use of low levels of the chemical compound 2,3,7,8-tetrachlorodibenzo-para-dioxin (TCDD) as a promoter blocker of specific identified cancers in men, specific identified cancers in women, prostate cancers in black men, and total cancers in each sex.

12 Claims, No Drawings

APPLICATION OF 2,3,7,8-TETRACHLORODIBENZO-PARA-DIOXIN (TCDD) AS A PROMOTER BLOCKER OF CANCER

This application is a continuation-in-part of Ser. No. 09/501,514, filed Feb. 9, 2000, now abandoned, which is is a continuation-in-part of Ser. No. 09/167,967, filed Oct. 8, 1998, now abandoned.

BACKGROUND OF THE INVENTION

This invention relates to the uses of the chemical compound 2,3,7,8-tetrachlorodibenzo-para-dioxin (TCDD) as a promoter blocker of specific identified cancers in men, specific identified cancers in women, prostate cancers in Black men, and overall cancers in each sex. A large body of significant scientific data on TCDD, including epidemiology studies, was developed as a result of early and continuing regulatory concern about TCDD's persistence in a wide variety of human tissues and its biological activity, often characterized as toxic at very low exposures. U.S. EPA, *Health Assessment Document for Polychlorinated Dibenzo-p-Dioxins* (1985); U.S. EPA, *Health Assessment Document for 2,3,7,8-Tetrachloro-dibenzo-p-dioxin (TCDD) and Related Compounds,* Volumes I, II and III (1994).

A cell which is "initiated" and then "promoted" becomes a cancer cell; once the cell replicates sufficiently, the cancer becomes diagnosable. This two-step cancer creation process, with some mutational involvement but without detailed specifications, has been taught for more than thirty years. A promoter blocker prevents the second, necessary step in the creation of a cancer cell.

TCDD is both a man-made and a naturally occurring chemical. U.S. EPA (1994). It is often a very minor contaminant in the chemical plant production of trichlorophenol, pentachlorophenol, hexachlorphene, and some salts, acids and esters of these compounds. Fingerhout et al., *Mortality Among U.S. Workers Employed in the Production of Chemicals Contaminated with 2,3,7,8-Tetrachlorodibenzo-p-dioxin (TCDD).* A NIOSH Report. (1990).

EPA has sought to regulate dioxin as a carcinogen on three occassions. In 1988, it succeeded in characterizing TCDD as a "possible" human carcinogen on the strength of significantly elevated liver cancer incidence in high dose female Sprague-Dawley rats fed TCDD over a lifetime. Kociba et al., *Toxicol. Appl. Pharmacol.* 46, 279–303 (1978). Neither Kociba et al. nor the Agency reported the low dose reduction in each sex—it was significant in the males—and, more importantly, the significant reduction in total cancers in each sex at the low and mid dose TCDD levels of 540 and 5100 parts per trillion (ppt) in liver tissue. Kociba et al. (1978); U.S. EPA (1985); and U.S. EPA (1994).

In 1994, EPA sought to regulate TCDD as a "probable" human carcinogen, using a population of 5280 male workers in 12 chemical plants, each of whom was exposed to contaminant levels of TCDD and some mix of 1000 unidentified other chemicals. Fingerhut et al. (1990). Fingerhut compared the cancer incidence in the plant workers to that expected in a national reference, and EPA concluded all the cancer incidence increases noted by Fingerhut were caused by the TCDD exposure and none were caused by exposures to other chemicals. U.S. EPA (1994). EPA's Science Advisory Board rejected the Agency's TCDD cancer claims. U.S. EPA Science Advisory Board, *Review of Draft Documents: A Second Look at Dioxin* (1995).

Again, in 2000, EPA reworked the criticized sections of its 1994 Report, relying mostly on reshaped and updated epidemiology data to remake its TCDD cancer claims, which the Agency's Science Advisory Board again rejected. U.S. EPA Science Advisory Board, *Review of Draft Documents: A Final Look at Dioxin* (2001).

Four patents have been issued on Beneficial antiestrogenic effects associated with exposure to TCDD-like or related compounds, none on TCDD. Bednarski U.S. Pat. No. 4,745,109; Morgan U.S. Pat. No. 4,732,904; Jones U.S. Pat. No. 4,418,068; and Safe U.S. Pat. No. 5,516,790. Indeed, Safe, whose chemical agents are most structurally similar to TCDD, specifically avoids claims on TCDD. Safe, citing Kociba's high dose female liver cancer data, observed that TCDD was anti-carcinogenic for mammary and uterine cancers, but at a body burden level so high (25,400 ppt) as to be very hepatocarcinogenic, and, therefore, therapeutically without value. The theory behind ass four patents is an anti-estrogenic effect, which is not the basis of this Inventor's claims.

A pair of research papers from DiGiovanni et al. (*Biochem. Biophys. Res. Com.* 86, 577–584 (1979); *Polynucl. Aromat. Hydrocarbons: Chem. Biol. Eff. Intl. Symp.* 4th (1980)) claim a very high single dose of TCDD significantly reduces an artificially elevated skin cancer incidence in several mice strains, when the YCDD dose is administered one to five days prior to the initiation of those cancers. No reduction in the elevated skin cancer incidence is observed when the TCDD is administered simultaneously with or a day after the skin cancer initiation step. In these papers no claim is made, or should be made by DiGiovanni, that the high level of TCDD administered reduces skin cancer occurence because of an effect on the promotional step in cancer creation. Still, the assertion might be made, by logical extension, that if TCDD is an initiator blocker for mouse skin at high dose, it might also reduce total cancer incidence in man by some other means at high dose. But the multiple step extension (mouse to man; skin to total cancer; and initiation to promotion) from DiGiovanni does not extend well to total cancer incidence in man: for example, Zober et al. (*Int. Arch. Occup. Environ. Health* 62, 139–157 (1990)) and Manz et al. (*Lancet* 338, 959–964 (1991)) in separate studies of different industrial cohorts observe a total cancer increase rather than the significant decrease expected from the "logical extension"; Steenland et al. (*J. Natl. Cancer Inst.* 91, 779–786 (1999)) finds a significant increase in total cancers in the most highly TCDD-exposed members of the NIOSH workforce that Fingerhut et al. reported on in 1990; over twenty years, Bertazzi et al. (*Amer. J. Epidem.* 153, 1031–1044 (2001)) finds a significant increase in total cancers among Italian men from Seveso in his pooled two highest exposed cohorts; and Flesch-Janys et al. (*Amer. J. Epidem.* 142, 1165–1174 (1995)) reports a significant increase in total cancer mortality among his most highly TCDD-exposed German herbicide chemical plant workers. These studies, individually and collectively, contradict any extension of the high TCDD-based diGiovanni teaching to total cancers in humans. These syudies collectively serve as a barrier to any claims of obviousness from diGiovanni. Further, this Invention is based on low, rather than high, body burden or exposure observations in humans and rats, and predicated on blocking the promotion step in cancer creation rather than the initiation step.

SUMMARY OF THE INVENTION

The proposed use of TCDD as a promoter blocker of cancers is new. TCDD is a well known chemical. In the past it has been manufactured and purified to 99% purity by the Dow Chemical Company. Kociba et al. (1978).

A careful analysis of the Kociba lifetime rodent feeding study shows theat TCDD body burdens of 540 and 5100 ppt are associated with a reduction of cancers at multiple tissue sites and overall in both male and female rats, a highly unusual and unexpected observation which the authors, EPA, and regulated industries failed to note. Kociba et al, (1978); U.S. EPA (1985 and 1994).

In addition to published and unpublished epidemiology data from the NIOSH Report (Fingerhut et al. (1990)), additional NIOSH Life Table records (LT20406 (1990)), and the Steenland et al. article (1999), the Inventor relies on Bertazzi et al.'s (*Epidemiol.* 4, 398–406 (1993)) cancer incidence data presentation on a residential population of men and women exposed to the lowest levels of TCDD as a result of a chemical plant explosion near Seveso, Italy, and the Inventor's own analysis of cancer incidence and body burden data in the Operation Ranch Hand (ORH) airmen exposed to TCDD as a result of service in Southeast Asia during the Vietnam War. None of the NIOSH and Seveso papers cited above claim that TCDD acts as an anti-carcinogen. The Air Force Scientists charged with developing the ORH Study also fail to observe TCDD as an anti-carcinogen. Ketchum et al. *Amer. J. Epidem.* 149, 630–639 (1999).

The ORH cancer incidence data collected over 30 years has particular value, because one may compute the cancer incidence effects associated with military service in Southeast Asia in internal cohorts unexposed or virtually unexposed to TCDD and distinguish them from an internal cohort of airmen exposed to TCDD within a well calibrated body burden range.

The Seveso Study (Bertazzi et al. (1993)) is a report on cancer incidence and cancer incidence changes in the first ten years following the population's exposure to TCDD and other chemicals. Over the course of these ten years, one expects not to register the carcinogenic effects of any chemicals acting as cancer initiators and to include any effects attributable to TCDD discernible within ten years, like promotion or promotion blocking. The first ten years of the lifetime NIOSH Study offer the same advantage. Fingerhut et al. (1990).

For a limited number of narrow cancer classifications, Bertazzi et al. (1993) has provided cancer incidence data stratified in five year intervals both for publication and as a courtesy to the Inventor. Kayajanian, *Ecotox. Environ. Safety* 42, 103–109 (1999). Fingerhut et al. (1990) also published five year cancer occurrence observations for total cancers. For several of the individual and total cancer classifications in Seveso's low exposure cohorts, a significant cancer incidence reduction is noted in the second five years when that value is compared to incidence in the first five years: primary liver cancer in men, corpus uteri and total cancers in women. Further, the incidence of total cancers in men in years 6–10 in the Fingerhut Report was significantly less than in years 1–5. This pattern of cancer incidence reduction in the second five year interval is what one would expect if TCDD acted as a promoter blocker of the enumerated individual cancer classifications and a sufficient number of other cancers to generate a significant total cancer incidence reduction. These other specific cancer classifications should include but not be limited to cancers in Seveso for which stratified cancer incidence data were not provided but where cancer incidence is significantly or notably reduced compared to the outside reference over the entire ten year period, like lung and multiple myeloma in men.

In the Inventor's analysis of ORH data, significant cancer incidence reductions are observed for skin and total cancers other than skin at mean TCDD body burden levels of 50–100 ppt. Kayajanian, *Ecotox. Environ. Safety* 46, 103–109 (2000); and Kayajanian, *Ecotox. Environ. Safety* (In press, 2001).

The incidence of soft tissue sarcoma (STS) and non Hodgkins lymphoma (NHL) in low exposure adults (men plus women) is significantly increased in the second five years in Seveso compared to the first five years. This pattern of cancer incidence change is what one would expect if TCDD acted as a promoter for these individual cancers, Fertazzi et al. (1993).

One of the plants (Midland) in the NIOSH Report has workers who reproduce the signature of individual cancer reductions and increases the Inventor observed in Seveso low exposure men: reductions in lung, primary liver (measured in Midland as liver) and multiple myeloma, which collectively are significant; and increases in STS and NHL, which individually are significant. The Seveso signature pattern of cancer incidence changes is present even though workers in Midland and the other 11 chemical plants were exposed to confounding chemicals which might have masked or diminished the extent of pattern confirmation. LT20406 (1990). From Steenland et al. (1999), one can estimate the TCDD level associated with the Midland plant wotkers as 105 ppt above background, or between 105 and 115 ppt.

To develop the Invention further, cross species comparisons are performed when no second epidemiology report is available to test the effect of TCDD exposure on women. For example, the Seveso stratified reductions in corpus uteri and total cancers in low exposure women are also observed in the low dose Kociba female rats, where uterine cancers ($p<0.06$) and total cancers ($p<0.01$) are significantly reduced. Kayajanian, *Regul. Toxicol. Pharmacol.* 26, 134–137 (1997).

The specific and total cancer reductions noted in the NIOSH, Seveso, and ORH studies can be tied to specific dioxin body burden levels measured in serum. Reading Steenland et al. (1999) and Fingerhut et al. (1990) together, one can estimate a range from 3 to 10,000 ppt extra TCDD in serum in eight of the 12 NIOSH plante worker cohorts. This range would be associated with the significant reduction in total cancers in the entire study in the second five years. Midland workers, who show the Seveso pattern of reductions of specific cancers, had 105 ppt TCDD above background, which is assumed to be 0 to 10 ppt.

The significant individual and total cancer reductions the Inventor noted from the Seveso data, whether stratified or not (Bertazzi et al. (1993)) are associated with median levels of 48 ppt TCDD. Bertazzi et al., *Amer. J. Epidem.* 153, 1031–1043 (2001). Measurement of TCDD levels include both men and women.

The ORH body burdens, cited above, associate significant skin cancer reductions in non black airmen with 100 ppt, and significant non skin cancer reductions with 50 ppt in all airmen. Kayajanian (2000)(In press, 2001). One standout cancer reduction is associated with an even lower TCDD body burden level: prostate cancer in black veterans is highest at non detect TCDD levels of less than 1.25 ppt; it is reduced at body burdens between 1.25 and 4.0 ppt, and lowest above 4.00 ppt, The pattern of prostate cancer reduction in black men is significant. Kayajanian, (In press, 2001).

All of the subjects in the three epidemiology studies cited above had involuntary exposures to TCDD which resulted in assayable TCDD levels associated with cancer reductions. Even though one may be unsure how much TCDD entered the body by each possible route in these studies, there are well documented methods of administering TCDD to rodents, other mammals and man that result in body burdens comparable to those biologically beneficial levels noted in the epidemiology studies. EPA devotes the first 71 pages of its TCDD Health Assessment Document (1994) to describing these methods. Poiger and Schlatter (*Chemosphere* 15,9–12 (1986)), in particular, describe the ingestion of tritiated TCDD in corn oil by a male volunteer, the 87% label retention (from which a body burden may be calculated), and the half-life for elimination. So, 87%, of the ingested TCDD added to the a 0–10 ppt level assumed for an administered subject would constitute the subject's "initial TCDD level."

TCDD persists in the human body for an extended period of time. In a pair of long term studies on ORH veterans, the half-life of TCDD in serum ranges from 5.8 to 9.6 years and from 10.0 to 14.1 years. Pirkle et al., *J. Toxicol. Environ. Health* 27, 165–171 (1989); and Wolfe et al., *J. Toxicol. Environ. Health* 41, 481–488 (1994). While the NIOSH data inform that a broad range of TCDD body burdens are effective in reducing total cancer incidence, when those data are properly read (Kayajanian, *Ecotox. Environ. Safety* (In press, 2001B), and Kociba reports data that associate total cancer reductions in each sex with TCDD levels of 540 and 5100 ppt, the more persuasive TCDD beneficial body burdens are bunched: 48 ppt from Seveso, 105–115 ppt from the Midland plant workers in the NIOSH Study, and 50–100 ppt from the ORH Study. For men, the Inventor would administer an "initial TCDD level" at the high end of the bunched range, and replentish it as necessary every five to ten years to reachieve that "initial TCDD level." In women, Seveso data reveal a range of 21 ppt to 71 ppt are associated with a significant total cancer incidence reduction. Needham et al., *Teratog. Carcinog. Mutagen.* 17. (4–5), 225–240 (1997–1998). The high end value would be the "initial TCDD level," and it should be replentished every five to ten years to reachieve that "initial TCDD level."

The 1994 EPA TCDD Health Assessment Document compiles other scientific information which informs the Invention:

(1) TCDD is found in a variety of tissues in many mammalian species, including man, where its half-life is about 7.4 years;

(2) TCDD preferentially binds to the aryl hydrocarbon (Ah) receptor, which is coded for by DNA; the TCDD-Ah complex binds to the aryl hydrocarbon nuclear translocator protein (Arnt); the TCDD-Ah-Arnt complex moves from the cytoplasm of a cell across the nuclear membrane into the nucleus to bind to DNA; and (3) TCDD has not been found to be mutagenic.

Kayajanian has observed that TCDD reduces cancer incidence percentagewise to a greater extent in men than in women, and in male rats to a greater extent than in female rats at the lowest study exposure. Kayajanian (1999).

By reference, the Inventor incorporates in this filing all the data tables in the 1994 EPA TCDD Health Assessment Document, Chapter 1, pages 1–71; he also incorporates any and all methods and data tables from the references cited above in this filing.

How might TCDD act as a promoter blocker to reduce cancer occurrence? A cancer cell often fails to adhere to cells like those from which it is derived; and after it has replicated, offspring sister cells often fail to adhere to each other. In addition, a cancer cell, unlike a normal cell, replicates seemingly without control by neighboring cells. If BOTH adhesion and replication were mediated through a membrane component, a cell membrane defect might simultaneously account for the alteration of both attributes.

In the explanation for how this Invention operates, each cell has in a nuclear chromosome a structural gene coding for the membrane component that allows the cell to attach to sister cells to form a tissue. Controling the activation of the structural gene are two elements, positioned with a left-to-right transcriptional direction, as noted in Formula 1*a*. The leftmost element in Formula 1*a* is an "off/on" switch; between that element and the structural gene is a blocking attachment site for the TCDD-Ah-Arnt complex.

FORMULAE 1*a* AND 1*b*

Models of TCDD'S Promotion Blocking and Promotion Activities

1*a*:  — ( $\frac{O/OS}{\dashrightarrow}$ )— ( $\underline{TCDDas}$ )— ( $\underline{\qquad MG \qquad \longrightarrow}$ )—

1*b*:  — ( $\frac{O/OS}{\dashrightarrow}$ )— ( $\underline{TCDDas}$ )— ( $\underline{\qquad MG \qquad X \longrightarrow}$ )—

Terms:
   O/OS="off/on" switch
  TCDD as=TCDD-Ah-Arnt complex attachment site
    MG=membrane gene
    X=defect in membrane gene
    ( )=extent of switch, attachment or gene site
    →=direction of transcription In a given tissue the "off/on" switch is usually turned "off." (Other membrane genes used by cells in other tissues are always turned "off" in the cells of this tissue.) When the switch is turned "on" during, say, membrane repair or cell growth and replication, the membrane gene is transcribed left-to-right coding a message for a gene product that becomes integrated into the cell membrane, provided the TCDD-Ah-Arnt complex is unavailable to block the transcription. In the absence of TCDD, no complex will form; at very low TCDD levels, the probability of the complex being available to block transcription is very low; as the cellular level of TCDD increases, so does the probability of the complex blocking transcription.

A mutation in the structural gene may have several consequences, one of which is the incorporation of an aberrant gene product into the cell membrane—a product which no longer allows the binding of that cell to sister cells (i.e., a cancer cell is created). Blocking the transcription of a mutant membrane structural gene stops the process that generates cancer. If the initial membrane gene mutation is taken as the initiating (or first) step in the formation of a cancer, and the turning "on" of the transcription of the defective membrane gene for cell replication or repair is taken as the promotional (or second) step, then Formula 1*b* illustrates how a TCDD complex can promote block the formation of a cancer cell in a variety of tissues.

Many of the tissue sites which exhibit cancer incidence reductions at modest TCDD levels, also exhibit cancer incidence increases at high TCDD levels. How might such a cancer incidence increase be explained using the understanding of the basic invention? The explanation does not require a structural gene mutation. At very low TCDD tissue concentrations, the TCDD-Ah-Arnt complex is available to block transcription of the membrane gene in only one or a few cells of the tissue. At much-higher-but-not-saturation levels, the complex is available to block all but one or a few cell transcriptions. During a developmental change in the tissue, when the "off/on" switch is turned "on" in all the cells of the tissue in the presence of TCDD below saturation level, a mixed tissue is generated. At the very low TCDD levels, all the cells but one or a few undergo a membrane structure change, leaving the unchanged cell(s) different from the vast majority; if the one or a few different cells do not adhere to their sister cell neighbors, it (they) may replicate without control to create a new tissue, i.e., act as a cancer cell. At the high-but-not-saturation TCDD level, the rare different cell is the one that undergoes the developmental change to become cancerous, because it is different from its sister cells. At intermediate TCDD levels, many of the cells undergo the developmental change and many do not, which generates a mixed tissue where each cell has a neighbor like itself to adhere to—so no cell acts as if it were different and cancerous.

DESCRIPTION OF THE PREFERRED EMBODIMENTS

There are a number of attributes associated with this Invention:

(1) Exposure to TCDD occurs through ingestion, injection, inhalation and the skin.

(2) At optimum levels, TCDD exposure significantly reduces total cancer incidence in both men and women, and in both male and female rats.

(3) At Optimum levels, TCDD exposure reduces cancer incidence at a number of tissue sites in men and women.

(4) In human studies, TCDD levels persist in the body, where the time required to reduce a specific body burden level within the optimum range to half that value is about 7.5 years.

(5) In human studies, TCDD body burden levels from 48 ppt to 1700 ppt have been associated with significant reductions in total and/or specific cancer reductions in men; in the single epidemiology study available on women, a TCDD body burden range of 21 ppt to 77 ppt has been tied to significant total and specific cancer reductions.

(6) TCDD acts as a promoter blocker, so its effective use may occur years after exposure to a cancer-initiating agent, (7) Cancer promotion may result from developmental changes in certain tissues.

(8) While a cancer benefit attaches to a broad range of TCDD body burdens in men, the most compelling epidemiology evidence of cancer reductions is associated with the lower portions of the range: Seveso, 48.0 ppt; the Midland plant workers of the NIOSH Study, around 105 ppt; and the airmen of the ORH Study, with a mean level of 195.7 ppt when they left Vietnam, but about 50 and 100 ppt when the cancers were avoided.

(9) Because TCDD persists, body burden levels can readily be increased, but not decreased.

While a cancer benefit would be expected to redound to most if not all adults maintaining an appropriate body burden level of TCDD, a number of evident situations exist where application of the Invention would generate a greater than average benefit.

EXAMPLE 1

Because TCDD exposure acts as a promoter blocker, its application can be targetted to specific individuals or populations exposed to cancer initiating agents, such as military exposed to burning gas and oil in the 1991 Mideast War or sun and skin irritants in Vietnam, residents of Chernobyl exposed on a continuing basis to cancer-causing radiation, cancer survivors who were exposed to cancer-causing agents to treat their existing cancers, and tobacco smokers and past smokers.

EXAMPLE 2

Because TCDD exposure acts as a promoter blocker years after the initiating event, TCDD exposure targetted to that event may be delayed until the time when promotion is likely to occur.

EXAMPLE 3

As men and women age, three changes become evident: cancer rates increase, beneficial developmental changes become less likely, and adverse developmental changes become more likely. Applying the Invention to older men and women should prevent cancers and more adverse developmental changes from occuring.

EXAMPLE 4

Because TCDD exposure is known to reduce cancer incidence in specific organ systems and TCDD may be introduced into the body by a variety of delivery systems, tailoring the delivery system and the site of TCDD administration should maximize body burden in the targetted tissue system.

What is claimed is:

1. A method of promotion blocking previously initiated cancer cells in men comprising administering TCDD thereto in an amount effective to produce an initial body burden within the range of 48ppt to 200ppt, and optionally replenishing to maintain a TCDD level in serum of 48 ppt to 200 ppt.

2. A method according to claim 1 when the cancer is of the respiratory system.

3. A method according to claim 1 when the cancer is lung cancer.

4. A method according to claim 1 when the cancer is liver and bilary cancer.

5. A method according to claim 1 when the cancer is primary liver cancer.

6. A method according to claim 1 when the cancer is multiple myeloma.

7. A method according to claim 1 when the cancer is basal, squamous and melanoma skin cancer.

8. A method of promotion blocking previously initiated prostate cancer cells in black men comprising administering TCDD thereto in an amount effective to produce an initial body burden within the range of 4.01 ppt to 200 ppt, and optionally replenishing to maintain a TCDD level in serum of 4.01 ppt to 200 ppt.

9. A method of promotion blocking previously initiated cancer cells in women comprising administering TCDD thereto in an amount effective to produce an initial body burden within the range of 21 ppt to 71 ppt, and optionally replenishing to maintain a TCDD level in serum at 21 ppt to 77 ppt.

10. A method according to claim 9 when the cancer is of the genitourinary organ system.

11. A method according to claim 9 when the cancer is uterine cancer.

12. A method according to claim 9 when the cancer is *corpus uteri* cancer.

* * * * *